United States Patent [19]
Fallot et al.

[11] Patent Number: 6,156,066
[45] Date of Patent: Dec. 5, 2000

[54] BREAST PROTHESIS

[76] Inventors: Sylvie Fallot; Zaki Ftaiha, both of 932 Merion Square Rd., Gladwyne, Pa. 19035

[21] Appl. No.: 09/338,902

[22] Filed: Jun. 10, 1999

Related U.S. Application Data

[63] Continuation of application No. 08/927,522, Sep. 11, 1997, abandoned.
[51] Int. Cl.⁷ ........................................ A61F 2/12
[52] U.S. Cl. .................................... 623/8; 623/7
[58] Field of Search ............................... 623/7, 8

[56] References Cited

U.S. PATENT DOCUMENTS

| | | | |
|---|---|---|---|
| 4,731,081 | 3/1988 | Tiffany | 623/8 |
| 5,545,221 | 8/1996 | Hang-Fu | 623/11 |
| 5,843,189 | 12/1998 | Perouse | 623/7 |
| 5,941,909 | 8/1999 | Purkait | 623/7 |
| 5,961,552 | 10/1999 | Iversen | 623/7 |

OTHER PUBLICATIONS

PCT/US/12394 Knapp, Terry R. Synthetic Triglyceride for Surgically Implanted Prostheses, Sep. 28, 1995.

*Primary Examiner*—Michael J. Milano

[57] ABSTRACT

A breast prosthesis envelope formed from flexible, non-absorbable material containing a filler material which is substantially shortening. Shortening composition is mainly any or a mixture of any of the following modified oils or fats such as derivatives of vegetable oil, soy bean oil, peanut oil, olive oil, cannula oil, and animal and human fat and approximately 10 percent laird have been found suitable for use.

7 Claims, No Drawings

BREAST PROTHESIS

This application is a continuation of Ser. No. 08/927,522 filing date Sep. 11, 1997 abandoned.

BACKGROUND OF THE INVENTION

The invention relates to the field of implant able breast prostheses, and in particular, filler materials for breast prostheses. Breast cancer has effected over 30 million women in the last 50 years. Recently, there has been a tremendous amount of research in developing breast prostheses which have minimal side effects on the human body even if the outer shell or envelope should rupture causing the filler to seep into other parts of the body. The silicon filled breast envelope has been the leading contributor to the disastrous paranoia in the field.

Saline solution has been determined to be the safest of filler materials. Unfortunately, saline solution produces an unnatural feel and look to the implant. The saline solution further has a low resistance to differences in pressure and drains gradually in about 10 years. The saline solution that enters the body has no adverse effects on the body. In addition, saline implants interfere with mammography of the breast, an important tool for detecting breast cancer.

In response to the failures of saline and silicon envelopes, there have been a number of attempts to make a prosthesis filled with organic filler that fulfilled the aesthetic characteristics provided by silicon solution yet gave the user the safe secure feeling provided by saline solution. The public reaction to the problems caused by silicon implants has generated a number of new implants directed to a safe filler material.

The patent to Destonet U.S. Pat. No. 4,995,882 introduced a breast prosthesis having a filler of peanut oil, sunflower seed oil, or any other material having an effective atomic number of 5.9 which is the atomic number of fat. The purpose of the filler is to permit the use of mammography in detecting tumors in patients having breast implants.

Other attempts to provide a safe filler material include cellulose gelling agents, collagen, starch and even honey. For example, U.S. Pat. No. 5,500,017 discloses a breast implant device using honey as a filler material. Brety, more particularly, discloses that high viscosity syrups used in breast implants hold their shape better and interfere less with mammography. In the event that the envelope used in the Brety implant should break, there are no studies on the effects of syrup inside the body. Moreover, the effective viscosity of the oil used in Destonet et al. or Brety fails to provide an implant that duplicates the natural breast.

SUMMARY OF THE INVENTION

This invention relates to a breast prosthesis containing filler comprised substantially of shortening. The invention also relates to a method of augmenting or reconstructing a human breast comprising the steps of heating shortening composition, and delivering the composition to an envelope positioned in the human breast to form a breast prosthesis or to have a shortening pre-filled and sealed implant similar to silicone filled implants. Shortening is biocompatible, will not adversely effect human tissue, and provides a firm life-like filler for an implant. The breast prostheses of the present invention have similar characteristics to the human breast. These breast prostheses may be used for breast augmentation or reconstruction and this implant will interfere minimally with mammography of the breast.

Accordingly, it is an object of the present invention to provide an implantable breast prosthesis which includes an outer shell which consists of a flexible, non-absorbable material and an inner composition which is comprised mainly of shortening.

DETAILED DESCRIPTION OF THE PREFERRED EMBODIMENT

The present invention provides a breast prothesis having a filler made from a solid substance. The invention relates to a breast prosthesis containing filler comprised substantially of shortening. Shortening is a solid fat made from unsaturated fat or oils that have been chemically transformed into a solid state through a modification process known as hydrogenation. During the hydrogenation procedure extra hydrogen atoms are pumped into unsaturated fat or oil, reducing the degree of unsaturation which raises the melting temperature range. This process eliminates unsaturation and leaves the chemical structure with a hydrocarbon chain containing no double bonds. A fat not having any double bond characteristics is by definition a saturated fat.

The solid state is achieved due to the saturation decreasing the flow rate of the fat, degree of saturation has an effect on viscosity. The more viscous a substance, the higher the resistance to flow. The decrease in flow rate raises the melting temperature because more energy or heat is required to break the bonds that are holding the chemical structure in the solid state. This results in shortening, a saturated fat, obtaining a solid state at room temperature. Comparably, unsaturated fats and oils obtain the liquid state at room temperature.

The breast prothesis is manufactured with an outer shell or envelope which can be made with any of a variety of suitable materials already in use. As those skilled in the art will appreciate, the prosthesis is implanted within a surgically created pocket, such a pocket may be created by the surgeon either directly under the beast tissue or underneath the chest wall muscle. Example of envelopes or shells are synthetic elastomers, silicone, nylon or any equivalent flexible, non-absorbable material.

The envelope is filled with a shortening composition. Shortening is defined as any modified oil or fat composition having solid state at room temperature. The envelope is implanted and the shortening composition is heated to increase the flow rate and lower the viscosity level to about 100 cp after which the composition is injected into the envelope using a syringe assembly. Once inside the envelope the temperature falls causing the viscosity of the composition to rise slowly, increasing the resistance to flow and settling in the solid state at body temperature.

Shortening compositions that have been found suitable for use include those compositions having at least 90 percent of any of the following modified oils or fats such as derivatives of vegetable oil, soy bean oil, olive oil, cannula oil, genetically altered cannula oil, animal and human fat. Shortening compositions having modified oil fat ingredients with a viscosity of at least 8000 cp. at body temperature manageable. The shortening composition is biocompatible with human beings and due to the solid state the chance of leakage is minimal even at body temperature.

Once the breast prosthesis has been implanted into the human breast and filled with the: heated composition, the composition cools to room temperature within a few hours. The normal activities of the human user of the subject breast prothesis and the rise of body temperature will cause the temperature of the prosthesis filler to change. After normal condition returns the filler changes back to solid state within hours to provide a prostheses that duplicates the natural breast.

What is claimed is:

1. A breast prosthesis comprising:
   an envelope made from a flexible, non absorbable material; and
   a filler material located within said envelope, wherein said filler material is a shortening composition.

2. The breast prosthesis according to claim 1, wherein said shortening composition is a vegetable oil derivative.

3. The breast prosthesis according to claim 1, wherein said shortening composition is a soy bean oil derivative.

4. The breast prosthesis according to claim 1, wherein said shortening composition is a peanut oil derivative.

5. The breast prosthesis according to claim 1, wherein said shortening composition is a derivative of olive oil.

6. The breast prosthesis according to claim 1 where said shortening composition is a derivative of canola oil.

7. The breast prothesis according to claim 1 where said shortening composition is a derivative of human fat.

* * * * *